United States Patent [19]

Eilingsfeld et al.

[11] Patent Number: 4,490,541

[45] Date of Patent: Dec. 25, 1984

[54] 5(3)-AMINOPYRAZOLO-3,4(4,5)-DICARBOXIMIDE AZO DYESTUFF INTERMEDIATES

[75] Inventors: Heinz Eilingsfeld; Karl-Heinz Etzbach, both of Frankenthal, Fed. Rep. of Germany

[73] Assignee: BASF Aktiengesellschaft, Lugwigshafen, Fed. Rep. of Germany

[21] Appl. No.: 456,095

[22] Filed: Jan. 6, 1983

[30] Foreign Application Priority Data

Feb. 11, 1982 [DE] Fed. Rep. of Germany ....... 3204713

[51] Int. Cl.³ .................................... C07D 487/02
[52] U.S. Cl. .................................... 548/370
[58] Field of Search .................................. 548/370

[56] References Cited

U.S. PATENT DOCUMENTS 3,166,571 1/1965 Izzo .................................... 548/370
3,526,633 9/1970 Gadekar ............................ 548/370

FOREIGN PATENT DOCUMENTS 1531071 11/1978 Fed. Rep. of Germany .

OTHER PUBLICATIONS

J. Org. Chem., 29, 1915-1979, (1964).

Primary Examiner—Henry R. Jiles
Assistant Examiner—Kurt G. Briscoe
Attorney, Agent, or Firm—Oblon, Fisher, Spivak, McClelland & Maier

[57] ABSTRACT

Compounds of the general formula I

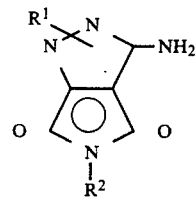

where $R^1$ is hydrogen, unsubstituted or substituted alkyl, cycloalkyl or aryl, acyl, alkoxycarbonyl, phenoxycarbonyl, unsubstituted or substituted carbamyl, thiocarbamyl or sulfamyl, or alkylsulfonyl or arylsulfonyl, and $R^2$ is hydrogen or a radical of a primary amine, are very useful as diazo components for the preparation of azo dyes.

3 Claims, No Drawings

5(3)-AMINOPYRAZOLO-3,4(4,5)-DICARBOXIMIDE AZO DYESTUFF INTERMEDIATES

The present invention relates to compounds of the general formula I

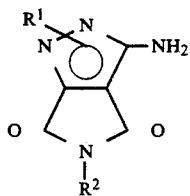

where $R^1$ is hydrogen, unsubstituted or substituted alkyl, cycloalkyl or aryl, acyl, alkoxycarbonyl, phenoxycarbonyl, unsubstituted or substituted carbamyl, thiocarbamyl or sulfamyl, or alkylsulfonyl or arylsulfonyl, and $R^2$ is hydrogen or a radical of a primary amine providing the imido nitrogen.

For example, $R^1$ is $C_1-C_{12}$-alkyl which may or may not be interrupted by oxygen or sulfur and can also be substituted by hydroxyl, $C_1-C_4$-alkoxy, phenyl, phenoxy, cyano or $C_1-C_{12}$-alkoxycarbonyl, or is cyclohexyl, $C_1-C_{12}$-alkanoyl, unsubstituted or substituted benzoyl, $C_1-C_4$-alkoxycarbonyl, phenoxycarbonyl, carbamyl, N,N-dialkylcarbamyl, N-arylcarbamyl, thiocarbamyl, sulfamyl, N,N-dialkylsulfamyl, N-arylsulfamyl, $C_1-C_4$-alkylsulfonyl, phenylsulfonyl or tolylsulfonyl, or is naphthyl or phenyl which is unsubstituted or substituted by fluorine, chlorine, bromine, $C_1-C_4$-alkyl, $C_1-C_4$-alkoxy, $C_1-C_4$-alkanoyl, nitro, benzoyl, cyano, $C_1-C_4$-alkoxysulfonyl, phenoxysulfonyl, hydroxysulfonyl, sulfamyl, $C_1-C_4$-alkoxycarbonyl, phenoxycarbonyl, carboxyl or carbamyl.

For example, $R^2$ is $C_1-C_{12}$-alkyl which may or may not be interrupted by oxygen or sulfur and can also be substituted by hydroxyl, $C_1-C_4$-alkoxy, $C_1-C_4$-alkanoyloxy, benzoyloxy, phenyl, phenoxy, cyano or $C_1-C_{12}$-alkoxycarbonyl, or is cyclohexyl, or is naphthyl or phenyl which is unsubstituted or substituted by fluorine, chlorine, bromine, $C_1-C_4$-alkyl, $C_1-C_4$-alkoxy, nitro, cyano, $C_1-C_4$-alkoxysulfonyl, phenoxysulfonyl, hydroxysulfonyl, $C_1-C_4$-alkoxycarbonyl, phenoxycarbonyl, carboxyl or carbamyl.

The compounds of the formula I can be prepared by reacting a compound of the formula II with a hydrazine of the formula III

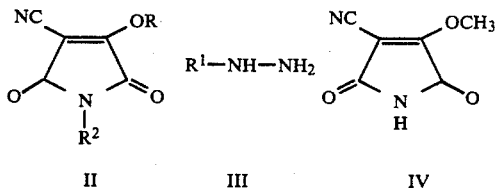

and subjecting the resulting hydrazone to a cyclization reaction. In the formula, R is a radical of an alcohol. It is also possible to introduce $R^1$ or $R^2$ subsequently into a hydrazone which is obtained as an intermediate and in which $R^1$ is H, or into a compound of the formula I where $R^1$ or $R^2$ is H.

Compounds of the formula II can be obtained by a method similar to that described in J.Amer.Chem.Soc. 80 (1958), 1385 for the compound of the formula IV.

The cyclization can be carried out, for example, by heating in a solvent, such as methanol, ethanol, propanol, butanol, methylglycol, ethylglycol, butylglycol, formic acid, acetic acid, propionic acid, sulfuric acid, phosphoric acid or toluenesulfonic acid.

Details on manufacture are given in the examples below, in which parts and percentages are by weight, unless stated otherwise.

The compounds of the formula I are very useful as diazo components for the preparation of azo dyes.

Of particular importance are compounds of the general formula Ia

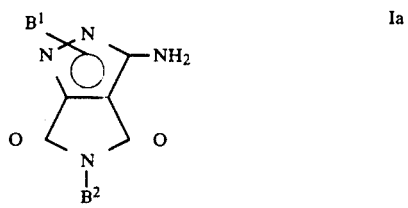

where $B^1$ is hydrogen, $C_1-C_4$-alkyl, cyanoethyl, cyclohexyl or $C_1-C_4$-alkanoyl, or is benzoyl which is unsubstituted or substituted by chlorine, cyano or nitro, or is $C_1-C_4$-alkoxycarbonyl or phenoxycarbonyl, or sulfamyl or carbamyl which is unsubstituted or N-monosubstituted or N,N-disubstituted by $C_1-C_4$-alkyl or phenyl, or is thiocarbamyl, $C_1-C_4$-alkylsulfonyl, phenylsulfonyl or tolylsulfonyl, or is naphthyl or phenyl which is unsubstituted or substituted by chlorine, cyano, nitro, methyl, methoxy, ethoxy, $C_1-C_4$-alkanoyl, benzoyl, $C_1-C_4$-alkoxycarbonyl, phenoxycarbonyl, carboxyl, $C_1-C_4$-alkoxysulfonyl or phenoxysulfonyl or by sulfamyl or carbamyl which is unsubstituted or N-monosubstituted or N,N-disubstituted by $C_1-C_4$-alkyl or phenyl, and $B^2$ is hydrogen, $C_1-C_8$-alkyl, cyclohexyl, allyl, $C_1-C_4$-alkoxy-$C_2-C_3$-alkyl, hydroxy-$C_2-C_3$-alkyl, phenoxy-$C_2-C_3$-alkyl, benzyl or phenylethyl, or is phenyl which is unsubstituted or substituted by chlorine, cyano or nitro.

In addition to the radicals mentioned above, specific examples of $B^1$ are methyl, ethyl, propyl, isopropyl, n-butyl, isobutyl, phenyl, naphthyl, o-, m- and p-nitrophenyl, o-, m- and p-cyanophenyl, o-, m- and p-chlorophenyl, 2,4-dinitrophenyl, 2,4-, 3,5- and 2,6-dichlorophenyl, p-methoxysulfonylphenyl, p-ethoxysulfonylphenyl, p-phenoxysulfonylphenyl, o-, m- and p-ethoxycarbonylphenyl, o-, m- and p-hydroxycarbonylphenyl, acetyl, propionyl, butyryl, benzoyl, methoxycarbonyl, ethoxycarbonyl, phenoxycarbonyl, N,N-dimethylcarbamyl, N-phenylcarbamyl, N,N-dimethylsulfamyl, N-phenylsulfamyl, methylsulfonyl, ethylsulfonyl and p-tolylsulfonyl, and specific examples of $B^2$ are methyl, ethyl, propyl, isopropyl, butyl, isobutyl, tert.-butyl, 2-methoxyethyl, 2-ethoxyethyl, 2-phenoxyethyl, 2-hydroxyethyl, phenyl, o-, m- and p-nitrophenyl, o-, m- and p-cyanophenyl and o-, m- and p-chlorophenyl.

EXAMPLE 1

(a) 2-Cyano-3-hydrazinomaleimide 50 parts of 2-cyano-3-methoxymaleimide are introduced into a solution of 16.5 parts of hydrazine hydrate in 300 parts by volume of isopropanol, while cooling with ice, the reaction mixture is then stirred at room temperature for half an hour, and the red precipitate is filtered off under suction, washed with isopropanol and dried. 47 parts (94% of theory) of 2-cyano-3-hydrazinomaleimide of melting point >350° C. are obtained. IR (KBr): 3120, 2200, 1670 cm$^{-1}$.

(b) 5-Aminopyrazolo-3,4-dicarboximide 30 parts of 2-cyano-3-hydrazinomaleimide in 100 parts by volume of glacial acetic acid are heated at the boil for seven hours, the mixture is then allowed to cool, and the precipitate is filtered off under suction, washed with a little glacial acetic acid and dried. 22 parts (73% of theory) of 5-aminopyrazolo-3,4-dicarboximide of melting point >350° C. are obtained. IR (KBr): 3300, 3120, 1670 cm$^{-1}$.

EXAMPLE 2

5-Aminopyrazolo-3,4-N-methyldicarboximide 16.6 parts of 2-cyano-3-methoxy-N-methylmaleimide are introduced into a solution of 5 parts of hydrazine hydrate in 80 parts by volume of n-butanol, while cooling with ice, the mixture is heated at the boil for four hours and then allowed to cool, and the resulting precipitate is filtered off under suction, washed with n-butanol and dried. 15 parts (94% of theory) of 5-aminopyrazolo-3,4-N-methyldicarboximide of melting point 285°–286° C. are obtained. IR (KBr): 3400, 3200, 1720, 1670 cm$^{-1}$.

The 2-cyano-3-methoxy-N-methylmaleimide required as the starting material is prepared as follows:

19 parts of the potassium salt of 2-cyano-3-hydroxy-N-methylmaleimide (prepared by a method similar to that for the salts described in J.Amer.Chem.Soc. 80 (1958), 3924) and 15.3 parts of phosphorus oxytrichloride in 100 parts by volume of heavy naphtha are heated at the boil for half an hour, the hot mixture is then filtered, the filtrate is allowed to cool, and the resulting precipitate is filtered off under suction, washed with gasoline and dried. 9.6 parts (56% of theory) of 2-cyano-3-chloro-N-methylmaleimide of melting point 141°–143° C. are obtained. IR (KBr): 2270, 1720, 1630 cm$^{-1}$.

43 parts of 2-cyano-3-chloro-N-methylmaleimide are introduced into 100 parts by volume of methanol, the mixture is heated at the boil for fifteen minutes and then cooled, and thereafter the precipitate is filtered off under suction, washed with a small amount of methanol and dried. 37 parts (88% of theory) of 2-cyano-3-methoxy-N-methylmaleimide of melting point 123°–125° C. are obtained. IR (KBr): 2220, 1720, 1640 cm$^{-1}$.

EXAMPLE 3

5-Amino-1-phenylpyrazolo-3,4-dicarboximide 50 parts of 2-cyano-3-methoxymaleimide are introduced into a solution of 35.6 parts of phenylhydrazine in 200 parts by volume of glacial acetic acid, while cooling with ice, the mixture is heated at the boil for 12 hours and then allowed to cool, and the precipitate is filtered off under suction, washed with a small amount of glacial acetic acid and dried. 61 parts (81% of theory) of 5-amino-1-phenylpyrazolo-3,4-dicarboximide of melting point 292°–294° C. are obtained. IR (KBr): 3440, 3220, 1670 cm$^{-1}$.

EXAMPLE 4

5-Amino-1-phenylpyrazolo-3,4-N-methyldicarboximide 22.8 parts of 5-amino-1-phenylpyrazolo-3,4-dicarboximide are dissolved in 100 parts by volume of dimethylformamide, 6 parts of a 30% strength solution of sodium methylate in methanol are then added, and the reaction mixture is stirred at room temperature for half an hour. 13.8 parts of dimethyl sulfate are then added, stirring is continued for a further four hours at room temperature, and precipitation is effected with 400 parts of water. The product is filtered off under suction, washed with water and dried. 19.5 parts (81% of theory) of 5-amino-1-phenylpyrazolo-3,4-N-methyldicarboximide of melting point 237°–239° C. are obtained. IR (KBr): 3400, 3200, 1720, 1640 cm$^{-1}$.

EXAMPLE 5

5-Amino-1-methylpyrazolo-3,4-N-methyldicarboximide

The title compound is prepared as described in Example 2, from 16.6 parts of 2-cyano-3-methoxy-N-methylmaleimide, 4.6 parts of methylhydrazine and 80 parts by volumne of n-butanol.

Yield: 13.2 parts (73% of theory).

Mp.: 240°–242° C.; IR (KBr): 3400, 3350, 3250, 1750, 1670, 1620 cm$^{-1}$.

EXAMPLE 6

5-Amino-1-acetylpyrazolo-3,4-N-methyldicarboximide 8.7 parts (84% of theory) of 2-cyano-3-(2'-acethydrazino)-N-methylmaleimide of melting point 220°–223° C. are obtained, as described in Example 1, from 8.3 parts of 2-cyano-3-methoxy-N-methylmaleimide and 3.7 parts of acethydrazide in 50 parts by volumne of isopropanol. IR(KBr): 3220, 2250, 1720, 1660 cm$^{-1}$.

When this product, in 40 ml of propionic acid, is heated at the boil for seven hours, it undergoes cyclization to give 5-amino-1-acetylpyrazolo-3,4-N-methyldicarboximide.

Yield: 6.8 parts (78% of theory).

Decomposition at 300° C.; IR (KBr): 3250, 1720, 1650 cm$^{-1}$.

We claim:

1. An aminopyrazole compound of the formula I

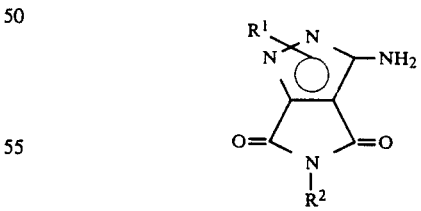

where $R^1$ is hydrogen, $C_1$–$C_{12}$-alkyl which may or may not be interrupted by oxygen or sulfur and can also be substituted by hydroxyl, $C_1$–$C_4$-alkoxy, phenyl, phenoxy, cyano or $C_1$–$C_{12}$-alkoxycarbonyl, or is cyclohexyl, $C_1$–$C_{12}$-alkanoyl, benzoyl which is unsubstituted or substituted by chlorine, cyano, or nitro, $C_1$–$C_4$-alkoxycarbonyl, phenoxycarbonyl, or sulfamyl or carbamyl which is unsubstituted or N-monosubstituted or N,N-disubstituted by $C_1$–$C_4$-alkyl or phenyl, thiocarbamyl, $C_1$–$C_4$-alkylsulfonyl, phenylsulfonyl or tolylsulfonyl, or is naphthyl or phenyl which is unsubstituted or substituted by fluorine, chlorine, bromine, $C_1$–$C_4$-alkyl, $C_1$–$C_4$-alkoxy, $C_1$–$C_4$-alkanoyl, nitro, benzoyl, cyano, $C_1$–$C_4$-alkoxysulfonyl, phenoxysulfonyl, hydroxysulfonyl, $C_1$–$C_4$-alkoxycarbonyl, phenoxycarbonyl, carboxyl or by sulfamyl or carbamyl which is unsubstituted or N-monosubstituted or N,N-disubstituted by $C_1$–$C_4$-alkyl or phenyl, and $R^2$ is hydrogen, $C_1$–$C_{12}$-alkyl which may or may not be interrupted by oxygen or sulfur and can also be substituted by hydroxyl, $C_1$–$C_4$-alkoxy, $C_1$–$C_4$-alkanoyloxy, benzoyloxy, phenyl, phenoxy, cyano, or $C_1$–$C_{12}$-alkoxycarbonyl, or is allyl, cyclohexyl, $C_1$–$C_4$-alkoxy-$C_2$–$C_3$-alkyl, hydroxy-$C_2$–$C_3$-alkyl, phenoxy-$C_2$–$C_3$-alkyl, benzyl, or phenylethyl, or is naphthyl or phenyl which is unsubstituted or substituted by fluorine, chlorine, bromine, $C_1$–$C_4$-alkyl, $C_1$–$C_4$-alkoxy, nitro, cyano, $C_1$–$C_4$-alkoxysulfonyl, phenoxysulfonyl, hydroxysulfonyl, $C_1$–$C_4$-alkoxycarbonyl, phenoxycarbonyl, carboxyl or carbamyl.

2. A compound of claim 1 where
$R^1$ is hydrogen, $C_1$–$C_4$-alkyl, cyanoethyl, cyclohexyl or $C_1$–$C_4$-alkanoyl, or is $C_1$–$C_4$-alkoxycarbonyl or phenoxycarbonyl, or is naphthyl or phenyl which is unsubstituted or substituted by chlorine, cyano, nitro, methyl, methoxy, ethoxy, $C_1$–$C_4$-alkanoyl, benzoyl, $C_1$–$C_4$-alkoxycarbonyl, phenoxycarbonyl, carboxyl, $C_1$–$C_4$-alkoxysulfonyl or phenoxysulfonyl, and $R^2$ is hydrogen, $C_1$–$C_8$-alkyl, cyclohexyl, allyl, $C_1$–$C_4$-alkoxy-$C_2$–$C_3$-alkyl, hydroxy-$C_2$–$C_3$-alkyl, phenoxy-$C_2$–$C_3$-alkyl, benzyl or phenylethyl, or is phenyl which is unsubstituted or substituted by chlorine, cyano or nitro.

3. A compound as claimed in claim 1, wherein both $R^1$ and $R^2$ are $C_1$–$C_{12}$-alkyl.

* * * * *